(12) United States Patent
Higgins

(10) Patent No.: US 10,779,983 B2
(45) Date of Patent: *Sep. 22, 2020

(54) COMPRESSION FOOT GARMENT, AND THERAPEUTIC METHOD FOR REDUCING HEEL PAIN

(71) Applicant: ING Source, Inc., Hickory, NC (US)

(72) Inventor: David B. Higgins, Newton, NC (US)

(73) Assignee: ING Source, Inc., Hickory, NC (US)

( * ) Notice: Subject to any disclaimer, the term of this patent is extended or adjusted under 35 U.S.C. 154(b) by 282 days.

This patent is subject to a terminal disclaimer.

(21) Appl. No.: 16/037,656

(22) Filed: Jul. 17, 2018

(65) Prior Publication Data

US 2018/0318123 A1 Nov. 8, 2018

Related U.S. Application Data

(63) Continuation of application No. 14/962,525, filed on Dec. 8, 2015, now Pat. No. 10,022,257, which is a
(Continued)

(51) Int. Cl.
*A61F 13/00* (2006.01)
*A61F 5/01* (2006.01)
(Continued)

(52) U.S. Cl.
CPC .............. *A61F 5/0127* (2013.01); *A41D 1/00* (2013.01); *A41D 1/22* (2013.01); *A41D 13/00* (2013.01);
(Continued)

(58) Field of Classification Search
CPC ....... A41B 11/00; A43B 17/00; A61F 5/0127; A61F 5/00; A61F 5/01; A61F 13/06;
(Continued)

(56) References Cited

U.S. PATENT DOCUMENTS 4,253,317 A 3/1981 Howard
5,617,745 A 4/1997 Della Corte
(Continued)

FOREIGN PATENT DOCUMENTS

DE 10 2006 032223 A1 7/2007

*Primary Examiner* — Kim M Lewis
(74) *Attorney, Agent, or Firm* — Schwartz Law Firm, P.C.

(57) ABSTRACT

A compression foot garment is integrally knit of a body yarn, and adapted for wear on a foot of a user. The foot garment incorporates first and second high compression zones, and a compression release zone between the high compression zones. The first high compression zone is adapted for applying substantially circumferential compression to the foot below the plantar fascia between the calcaneus and metatarso-phalangeal joints and generally around the midfoot. The second high compression zone is adapted for applying substantially circumferential compression to the foot above the calcaneus and generally around an ankle of the user. The first and second high compression zones may comprise elastic yarns integrated with the body yarn. The compression release zone is adapted for applying reduced compression to the foot in an area between the first and second high compression zones.

16 Claims, 6 Drawing Sheets

Related U.S. Application Data continuation of application No. 13/880,772, filed as application No. PCT/US2012/062363 on Oct. 29, 2012, now Pat. No. 9,204,986.

(60) Provisional application No. 61/628,349, filed on Oct. 28, 2011.

(51) Int. Cl.

| | | |
|---|---|---|
| *A41D 1/00* | (2018.01) | |
| *A41D 13/05* | (2006.01) | |
| *A61F 13/06* | (2006.01) | |
| *A61F 5/00* | (2006.01) | |
| *A41D 13/00* | (2006.01) | |
| *A61F 7/02* | (2006.01) | |
| *A61F 7/00* | (2006.01) | |
| *A41D 1/22* | (2018.01) | |
| *A61F 13/08* | (2006.01) | |

(52) U.S. Cl.
CPC ......... *A41D 13/05* (2013.01); *A41D 13/0543* (2013.01); *A61F 5/00* (2013.01); *A61F 5/01* (2013.01); *A61F 5/0111* (2013.01); *A61F 7/00* (2013.01); *A61F 7/02* (2013.01); *A61F 13/06* (2013.01); *A61F 13/064* (2013.01); *A61F 13/065* (2013.01); *A61F 13/066* (2013.01); *A61F 13/067* (2013.01); *A61F 13/069* (2013.01); *A61F 13/08* (2013.01)

(58) Field of Classification Search
CPC .... A61F 13/064; A61F 13/065; A61F 13/068; A61F 13/08; A41D 1/00
USPC .......................................................... D2/980
See application file for complete search history.

(56) References Cited

U.S. PATENT DOCUMENTS

| | | |
|---|---|---|
| 7,192,411 B2 | 3/2007 | Gobet et al. |
| 7,434,423 B1 | 10/2008 | Reid, Jr. |
| 7,934,267 B2 | 5/2011 | Nordstrom |
| 8,221,340 B2 | 7/2012 | Farrow |
| 8,317,736 B2 | 11/2012 | Virkus |
| 9,204,986 B2 | 12/2015 | Higgins |
| 10,022,257 B2 | 7/2018 | Higgins |
| 2003/0230121 A1 | 12/2003 | Yokoyama |
| 2006/0085894 A1 | 4/2006 | Yakopson et al. |
| 2006/0247566 A1 | 11/2006 | Gobet |
| 2009/0165190 A1 | 7/2009 | Araki |
| 2011/0015668 A1* | 1/2011 | Cros ...................... D04B 1/265 606/201 |
| 2012/0102613 A1* | 5/2012 | Loth .................. A41D 13/0543 2/22 |
| 2012/0180195 A1 | 7/2012 | Shull |
| 2013/0131572 A1* | 5/2013 | Cros ......................... A61F 5/40 602/75 |
| 2013/0263629 A1 | 10/2013 | Gaither |
| 2017/0049631 A1* | 2/2017 | Slaski .................. A61F 5/0111 |

\* cited by examiner

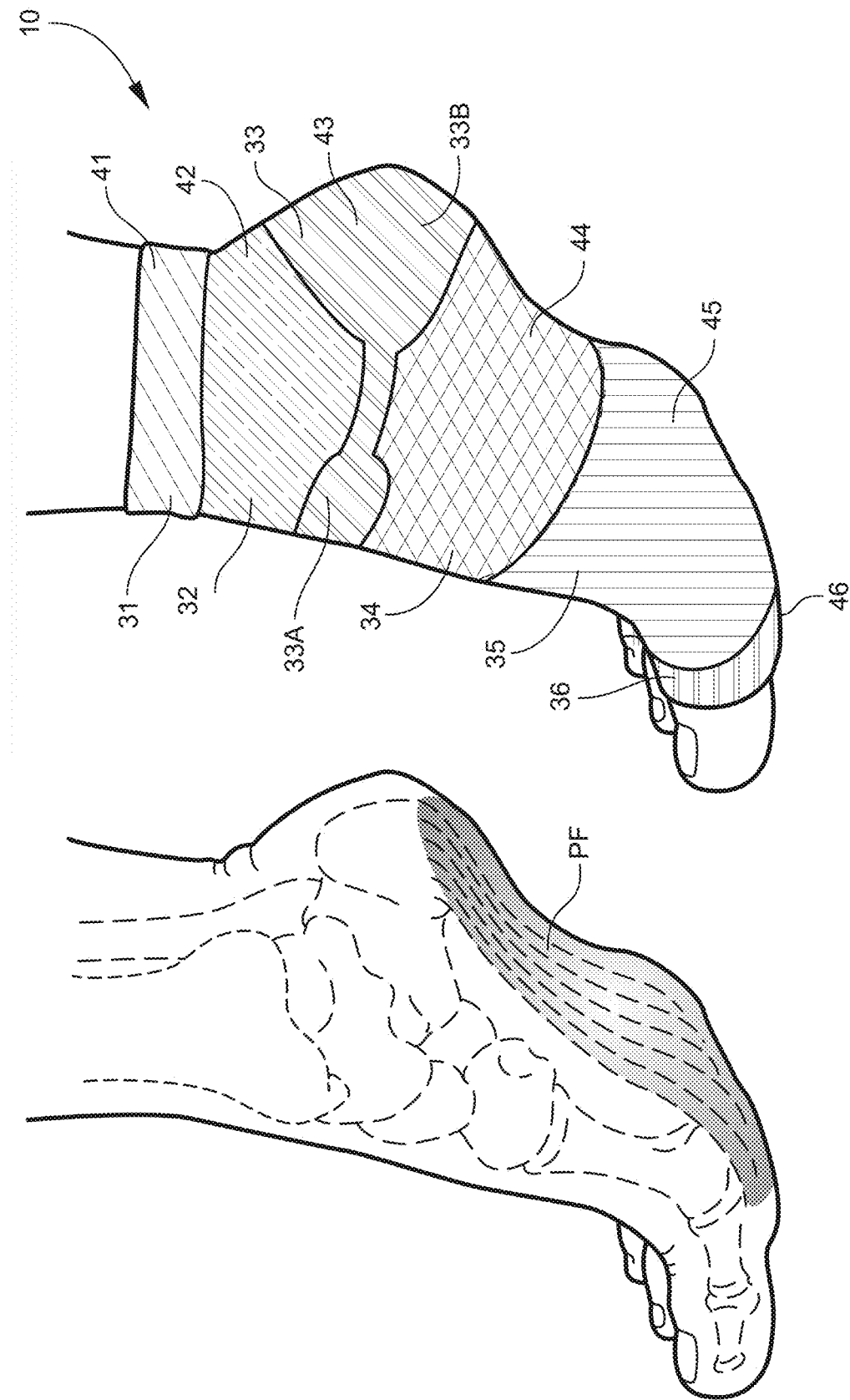

COMPRESSION FOOT GARMENT, AND THERAPEUTIC METHOD FOR REDUCING HEEL PAIN

TECHNICAL FIELD AND BACKGROUND OF THE DISCLOSURE

The present disclosure relates broadly and generally to foot supports, such as those used for general medical purposes to address conditions associated with edema (swelling), arch weakness, and heel pain resulting from injury to the plantar fascia ligaments. The plantar fascia is the thick connective tissue which supports the arch on the bottom of the foot. It runs from the tuberosity of the calcaneus (or heel bone) forward to the heads of the metatarsal bones—the bone between each toe and the bones of the mid foot. The often painful condition plantar fasciitis is an inflammatory condition of the plantar fascia. This can happen from injury, physical stress, or sometimes for no obvious reason. The most common point for this inflammation is where this ligament joints the heel bone.

SUMMARY OF EXEMPLARY EMBODIMENTS

Various exemplary embodiments of the present invention are described below. Use of the term "exemplary" means illustrative or by way of example only, and any reference herein to "the invention" is not intended to restrict or limit the invention to exact features or steps of any one or more of the exemplary embodiments disclosed in the present specification. References to "exemplary embodiment," "one embodiment," "an embodiment," "various embodiments," and the like, may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

It is also noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

According to one exemplary embodiment, the present disclosure comprises a compression foot garment or "sleeve" integrally knit of a body yarn (e.g., in circumferential courses and axial wales), and is adapted for wear on a foot of a user. The foot of the user comprises a calcaneus, a midfoot, metatarso-phalangeal joints, and a plantar fascia extending below the midfoot between the calcaneus and metatarso-phalangeal joints. The portions of the foot and foot anatomy are listed herein to provide antecedent basis for certain functional language recited below. This listing is not intended to limit application of the exemplary foot garment only to these portions of the foot, as parts of the foot garment in other embodiments may extend around or cover other portions of the foot and leg.

The exemplary foot garment incorporates first and second circumferential high compression zones, and a compression release zone between the high compression zones. The first high compression zone is adapted for applying substantially circumferential compression to the foot below the plantar fascia between the calcaneus and metatarso-phalangeal joints and generally around the midfoot. The second high compression zone is adapted for applying substantially circumferential compression to the foot above the calcaneus and generally around an ankle of the user. The first and second high compression zones may comprise elastic yarns integrated (e.g., laid-in or knitted) with the body yarn. The compression release zone is adapted for applying reduced compression to the foot in an area between the first and second high compression zones. In one exemplary embodiment, the first and second high compression zones reside directly adjacent the compression release zone on opposite sides of the compression release zone. The term "directly adjacent" in this context means a fabric area (or "zone") located or formed beside or surrounded, in whole or in part, by another fabric area (or "zone") without intervening fabric, parts or other structure.

The term "foot garment" refers broadly herein to any hosiery or other fabric construction designed to cover at least a portion of the wear's foot. The foot garment may be knit in whole or in part (e.g., using conventional circular knitting machinery), and may be specially designed for a variety of uses including running, cycling, hiking, golf, hunting, and other general athletic and every-day wear. The present foot garment may comprise (or be integrally formed with) an open-toe sleeve, foot wrap, footsock, tube sock, calf-high sock, mid-calf or over-the calf sock, crew sock, stocking, stretch or support hosiery, or the like.

According to another exemplary embodiment, the first high compression zone comprises elastic yarns adapted for applying course-to-course graduated compression to the foot of the user increasing in an axial direction towards a toe end of the garment. The term "axial" or "axial direction" refers herein to mean extending along a generally linear notional axis passing through circumferential portions (e.g., courses) of the garment. For example, the respective compression zones of the exemplary foot garment may be axially divided—or divided along a generally vertical length (such as from the heel upwardly towards the ankle or lower leg) and/or a generally horizontal length (such as from the heel towards the toe).

According to another exemplary embodiment, the second high compression zone comprises elastic yarns adapted for applying course-to-course graduated compression to the foot of the user increasing in an axial direction towards a leg end of the garment.

According to another exemplary embodiment, the first and second high compression zones apply substantially equal compression to the foot of the user. In other words, neither zone applies substantially more or less compression to the foot than the other. The term "substantially equal" in this context is defined herein to mean within +/−10 percent.

According to another exemplary embodiment, each of the first and second high compression zones applies greater than 20 mmHg of compression to the foot of the user, and the compression release zone applies less than 15 mmHg of compression to the foot of the user.

According to another exemplary embodiment, the first and second high compression zones comprise a substantially equal number of circular-knit courses. In this context, the term "substantially equal" means within +/−10 percent.

According to another exemplary embodiment, the compression release zone comprises a reduced compression heel pocket formed between the first and second high compression zones.

According to another exemplary embodiment, the compression release zone is adapted to extend over a top of the foot proximate an ankle joint of the wearer. This area of the release zone may be substantially oval, and may be entirely devoid of elastic yarns. In one exemplary embodiment, this oval area of the release zone is approximately 2.0-3.0 inches in length and approximately 0.5 to 1.0 inches wide.

According to another exemplary embodiment, a moderate compression zone is formed adjacent the first high compression zone, and extends axially towards a toe end of the garment. The moderate compression zone is adapted for applying reduced circumferential compression to the foot between the first high compression zone and the toe end of the garment. In this exemplary embodiment, the moderate compression zone may be formed directly adjacent the first high compression zone. The term "directly adjacent" in this context means a fabric area (or "zone") located or formed beside or surrounded, in whole or in part, by another fabric area (or "zone") without intervening fabric, parts or other structure.

According to another exemplary embodiment, the moderate compression zone comprises elastic yarns integrated with the body yarn, and adapted for applying course-to-course graduated compression to the foot of the user increasing in an axial direction towards the toe end of the garment. Graduated compression may be achieved by laying-in elastic yarns of strategic lengths.

According to another exemplary embodiment, the moderate compression zone applies between 10%-50% less compression to the foot as compared to the compression applied by the first and second high compression zones.

According to another exemplary embodiment, each of the first and second high compression zones and moderate compression zone comprise a substantially equal number of circular-knit courses. In this context, the term "substantially equal" means within +/−10 percent of each other.

According to another exemplary embodiment, a light compression zone resides adjacent the moderate compression zone at the toe end of the garment. In this exemplary embodiment, the light compression zone may be formed directly adjacent the moderate compression zone. The term "directly adjacent" in this context means a fabric area (or "zone") located or formed beside or surrounded, in whole or in part, by another fabric area (or "zone") without intervening fabric, parts or other structure.

According to another exemplary embodiment, the light compression zone comprises a flat-knit toe welt (or toe closure).

According to another exemplary embodiment, a light compression zone resides adjacent the second high compression zone at a leg end of the garment. In this exemplary embodiment, the light compression zone may be formed directly adjacent the second high compression zone. The term "directly adjacent" in this context means a fabric area (or "zone") located or formed beside or surrounded, in whole or in part, by another fabric area (or "zone") without intervening fabric, parts or other structure.

According to another exemplary embodiment, the light compression zone at the leg end of the garment comprises a folded ankle welt.

In yet another exemplary embodiment, the present disclosure comprises a therapeutic method for reducing heel pain. The method includes applying a compression foot garment to a foot of user. As indicated above, the foot comprises a calcaneus, a midfoot, metatarso-phalangeal joints, and plantar fascia extending below the midfoot between the calcaneus and metatarso-phalangeal joints. The compression foot garment is worn by the user to stretch and support the plantar fascia, such that a first high compression zone of the foot garment applies substantially circumferential compression to the foot between the calcaneus and metatarso-phalangeal joints and generally around the midfoot; and a second high compression zone applies substantially circumferential compression to the foot above the calcaneus and generally around an ankle of the user; and a compression release zone between the first and second high compression zones applies reduced compression to the foot in an area between the first and second compression zones.

The term "therapeutic" is used broadly herein to mean of or pertaining to the health of the foot, or treatment of a foot condition.

BRIEF DESCRIPTION OF THE DRAWINGS

Exemplary embodiments of the present invention will hereinafter be described in conjunction with the following drawing figures, wherein like numerals denote like elements, and wherein:

FIG. 6 is a further view showing the anatomy of the foot in phantom with the plantar fascia ligaments shaded; and FIG. 7 shows the exemplary foot garment applied to the foot in FIG. 7.

DESCRIPTION OF EXEMPLARY EMBODIMENTS AND BEST MODE

The present invention is described more fully hereinafter with reference to the accompanying drawings, in which one or more exemplary embodiments of the invention are shown. Like numbers used herein refer to like elements throughout. This invention may, however, be embodied in many different forms and should not be construed as limited to the embodiments set forth herein; rather, these embodiments are provided so that this disclosure will be operative, enabling, and complete. Accordingly, the particular arrangements disclosed are meant to be illustrative only and not limiting as to the scope of the invention, which is to be given the full breadth of the appended claims and any and all equivalents thereof. Moreover, many embodiments, such as adaptations, variations, modifications, and equivalent arrangements, will be implicitly disclosed by the embodiments described herein and fall within the scope of the present invention.

Although specific terms are employed herein, they are used in a generic and descriptive sense only and not for purposes of limitation. Unless otherwise expressly defined herein, such terms are intended to be given their broad ordinary and customary meaning not inconsistent with that applicable in the relevant industry and without restriction to any specific embodiment hereinafter described. As used herein, the article "a" is intended to include one or more items. Where only one item is intended, the term "one", "single", or similar language is used. When used herein to join a list of items, the term "or" denotes at least one of the items, but does not exclude a plurality of items of the list.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Additionally, any references to advantages, benefits, unexpected results, or operability of the present invention are not intended as an affirmation that the invention has been previously reduced to practice or that any testing has been performed. Likewise, unless stated otherwise, use of verbs in the past tense (present perfect or preterit) is not intended to indicate or imply that the invention has been previously reduced to practice or that any testing has been performed.

Figure 1:
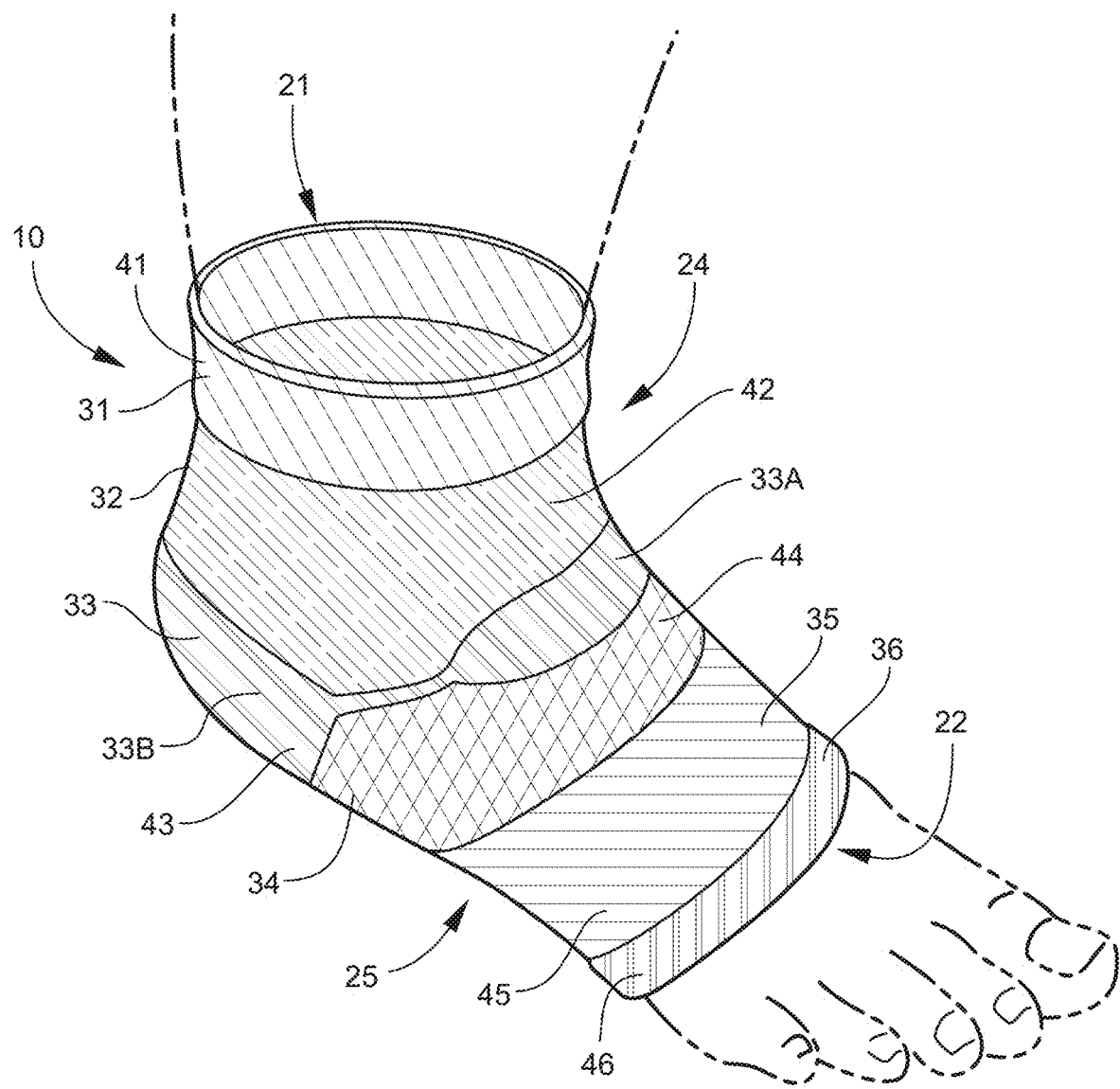
FIG. 1 is a perspective view of a compression foot garment according to one exemplary embodiment of the present disclosure, and showing the garment applied to a foot of wearer in phantom.
Figure 2:
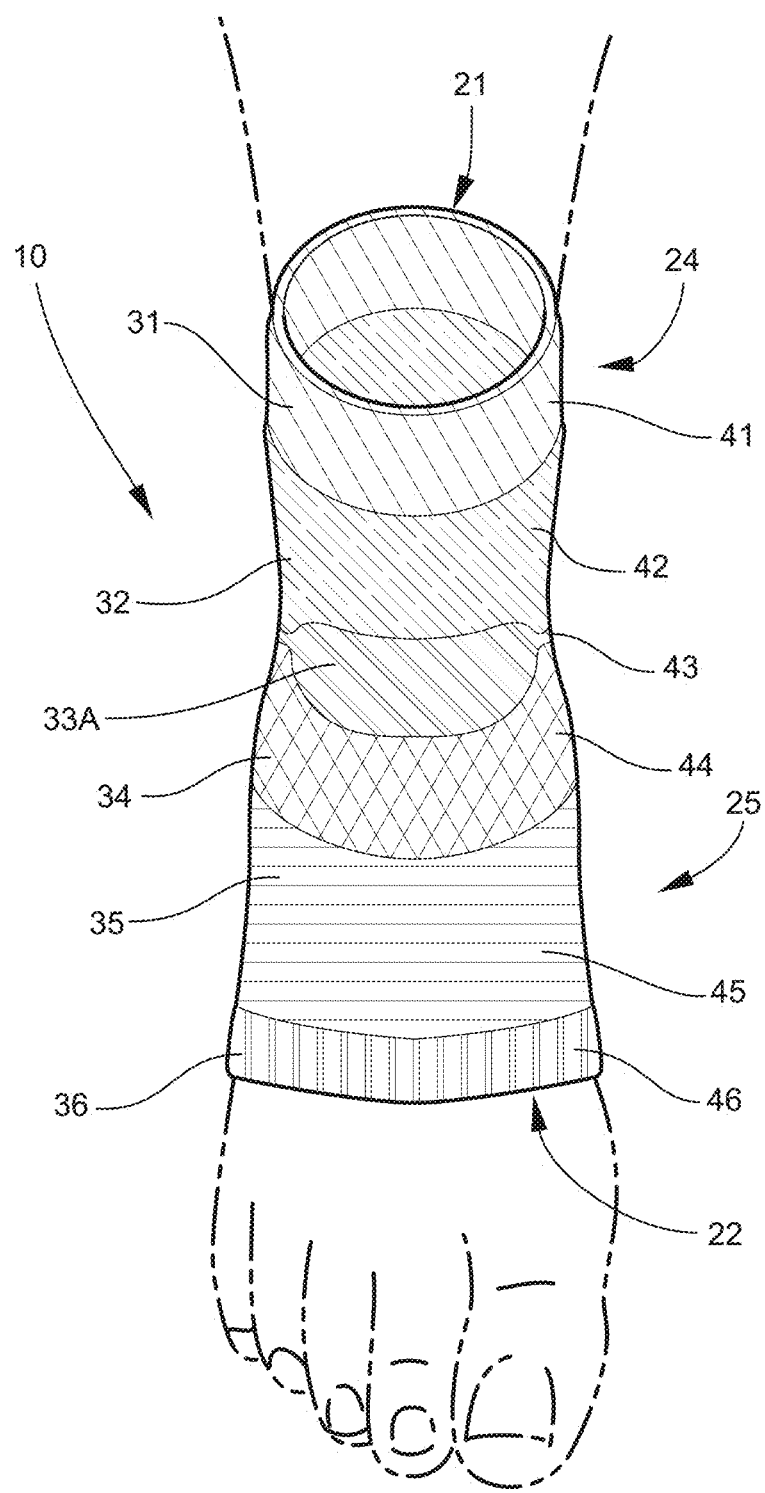
FIG. 2 is a top view of the exemplary compression foot garment showing the garment applied to a foot of wearer in phantom.
Figure 3:
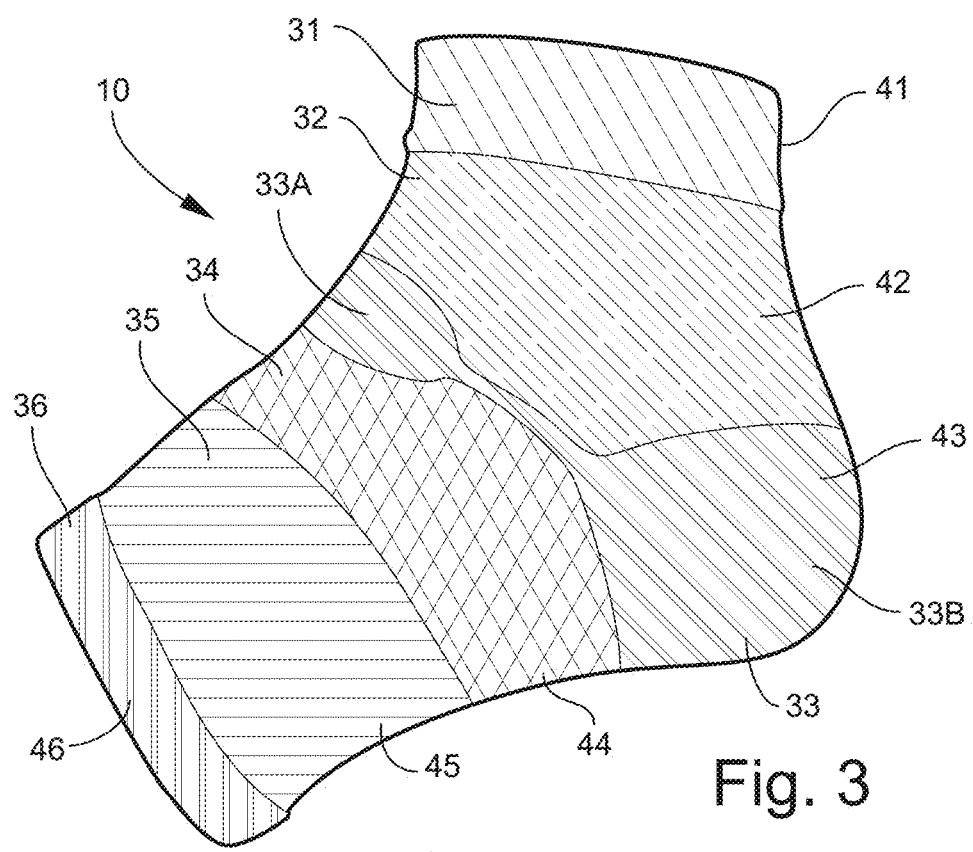
FIGS. 3 and 4 are respective side views of the exemplary foot garment removed from the wearer in a relaxed condition.
Figure 4:
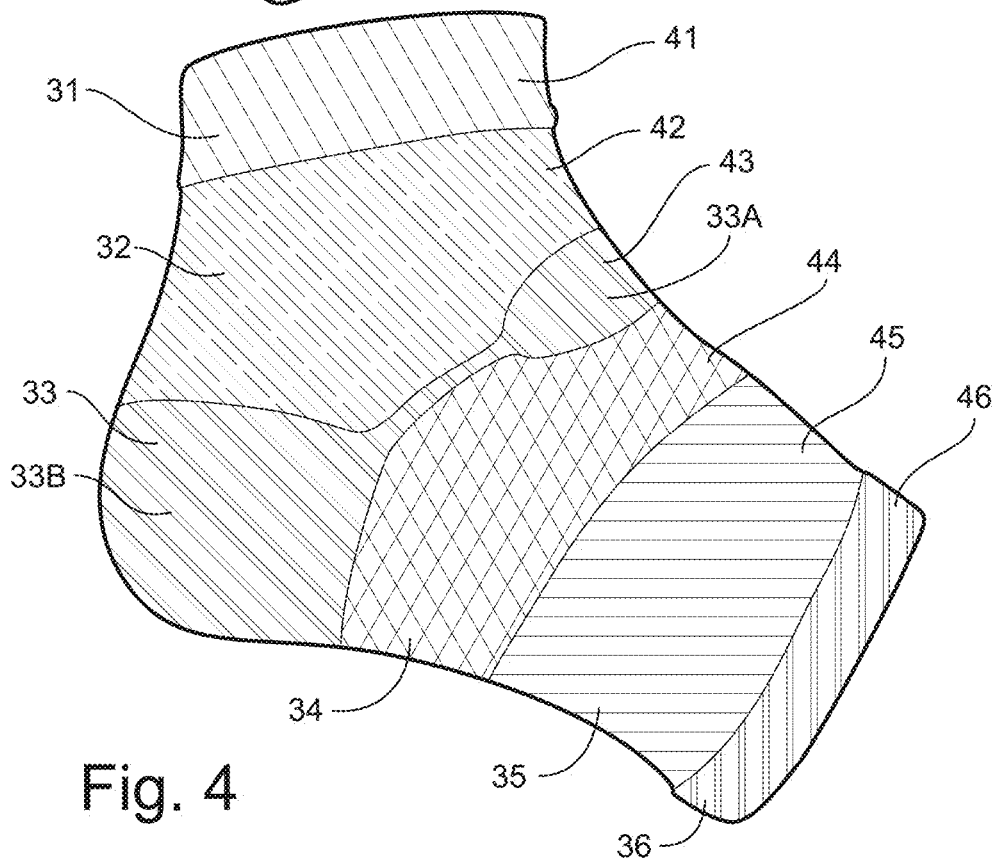

Referring now specifically to the drawings, a one-piece compression foot garment according to one exemplary embodiment of the present disclosure is illustrated in FIG. 1, and shown generally at reference numeral 10. The exemplary foot garment 10 may be formed throughout of a closed-loop Jersey-knit body yarn comprising micro-nylon, moisture wicking fibers, and/or other natural or synthetic fibers or fiber blends. Elastic yarns, such as a spandex or other elastomer, are laid-in the body yarn in predetermined areas of the foot garment 10 to create multiple distinct zones of predetermined compression. One exemplary construction comprises approximately 76% 140-denier micro-nylon and 24% 280-denier LYCRA® spandex. As described further below, the compression zones are intended to lift (or stretch) and support the plantar fascia "PF" of the wearer (FIG. 6), thereby reducing heal pain caused by inflammation or injury to these ligaments of the foot—an ailment referred to as plantar fasciitis. In the exemplary embodiment, the present foot garment 10 may be constructed on a circular hosiery knitting machine integrating a plurality of yarns formed in needle and sinker loops extending in circumferential courses and axial wales.

One commercial example of a circular knitting machine capable of producing the present foot garment 10 may be the "CC4-MED" machine manufactured by Merz Maschinenfabrik GmbH of Hechingen, Germany. The CC4-MED comprises a 4-feed, high-efficiency, single-cylinder circular knitting machine with appliance reciprocated heel for the production of various compression garments in compression classes I to III. As represented by Merz, the appliance reciprocated heel allows the knitting-in of a reciprocated heel, and optionally a reciprocated toe. The Merz positive feeders enable the feeding-in of inlay yarns to produce the desired compression with controlled feed-in yarn tension in each mesh course. An integrated double-welt appliance allows the knitting of double-welts, elastic welts and double-toes. Alternatively, the exemplary foot garment 10 may be fabricated according to other known techniques, such as by cut-and-sew of elasticized fabric from pre-designed patterns, with flat lock stitching.

Referring to FIGS. 1-4, the exemplary foot garment 10 comprises ankle and toe welts 21, 22 (or fabric closures) at respective open leg and toe ends of the garment 10, and integrally-knit ankle and foot portions 24 and 25 divided into axially adjacent circumferential regions. These circumferential regions may be designated as upper ankle region 31, lower ankle region 32, heel and upper instep region 33, rear sole and mid-instep region 34, front sole and lower instep region 35, and open toe region 36. The exemplary garment regions generally define respective therapeutic zones 41, 42, 43, 44, 45, and 46 of designated compression designed to closely and comfortably fit the garment 10 to the wearer, while strategically supporting, lifting, and gently stretching the plantar fascia "PF". The zones 41-46 are uniquely crosshatched in the drawings in order to readily distinguish one zone from another.

Figure 5:
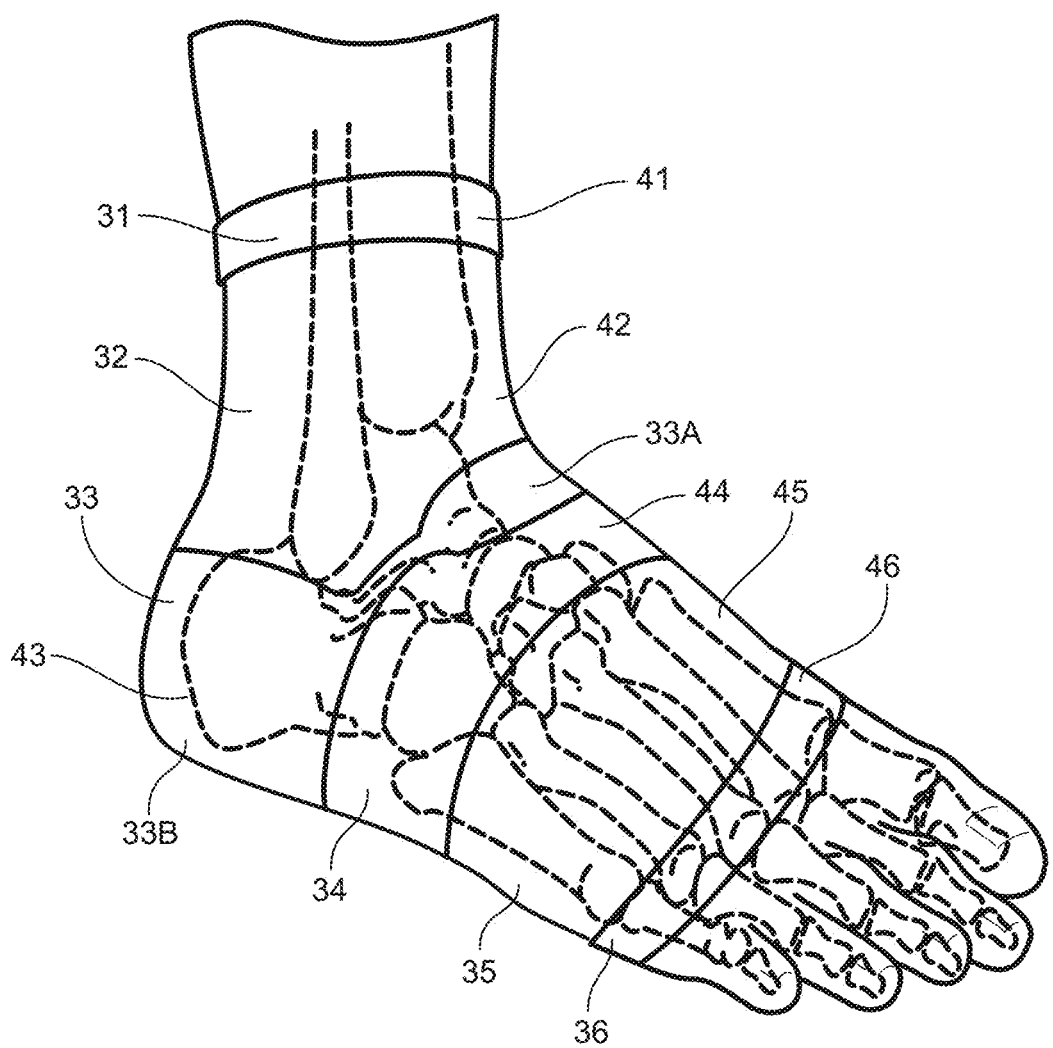
FIG. 5 is a side view of the exemplary foot garment applied to the wearer, and showing the anatomy of the foot in phantom.

As best shown in FIG. 5, the circumferential zones 41-46 of the exemplary foot garment 10 are located to apply predetermined degrees of compression to various parts of the foot. In one embodiment, zones 42 and 44 of the foot garment 10 comprises respective high compression zones. The first high compression zone 44 functions to apply substantially circumferential compression to the foot between the calcaneus and metatarso-phalangeal joints and generally around the midfoot. The second high compression zone 42 applies substantially circumferential compression to the foot above the calcaneus (proximate the Achilles tendon) and generally around a lower ankle of the wearer. These zones 42, 44 in particular cooperate to support and lift the foot to gently stretch the plantar fascia "PF" ligaments, as demonstrated in FIGS. 6 and 7.

Zone 43 comprises a compression release zone between and directly adjacent the high compression zones 42 and 44, and serves to apply reduced compression to the foot at the heel and upper instep region 33. The area of the release zone 43 at the upper instep region 33A may be substantially oval-shaped with a relaxed dimension of approximately is approximately 2.0-3.0 inches in length and approximately 0.5 to 1.0 inches wide. Exemplary zone 45 comprises a moderate compression zone directly adjacent the high compression zone 44, and extending axially towards a toe end of the garment 10. This zone 45 is designed to cover an area of the foot around the metatarsal bones. Zones 41 and 46 comprise first and second light compression zones at the ankle and toe welts 21, 22 of the garment 10, respectively. The first light compression zone 41 is located directly adjacent high compression zone 42, and resides at the upper ankle of the wearer forming the ankle welt 21. The ankle welt 21 may be folded and stitched to form a double-layer fabric closure, and may be devoid of elastic fibers on the inside layer to reduce pressure and thickness around the ankle. The second light compression zone 46 is located directly adjacent the moderate compression zone 45, and is designed to reside proximate the metatarso-phalangeal joints of the wearer forming the toe welt 22. The toe welt 22 may comprise a single-layer flat knit construction.

Figure 8:
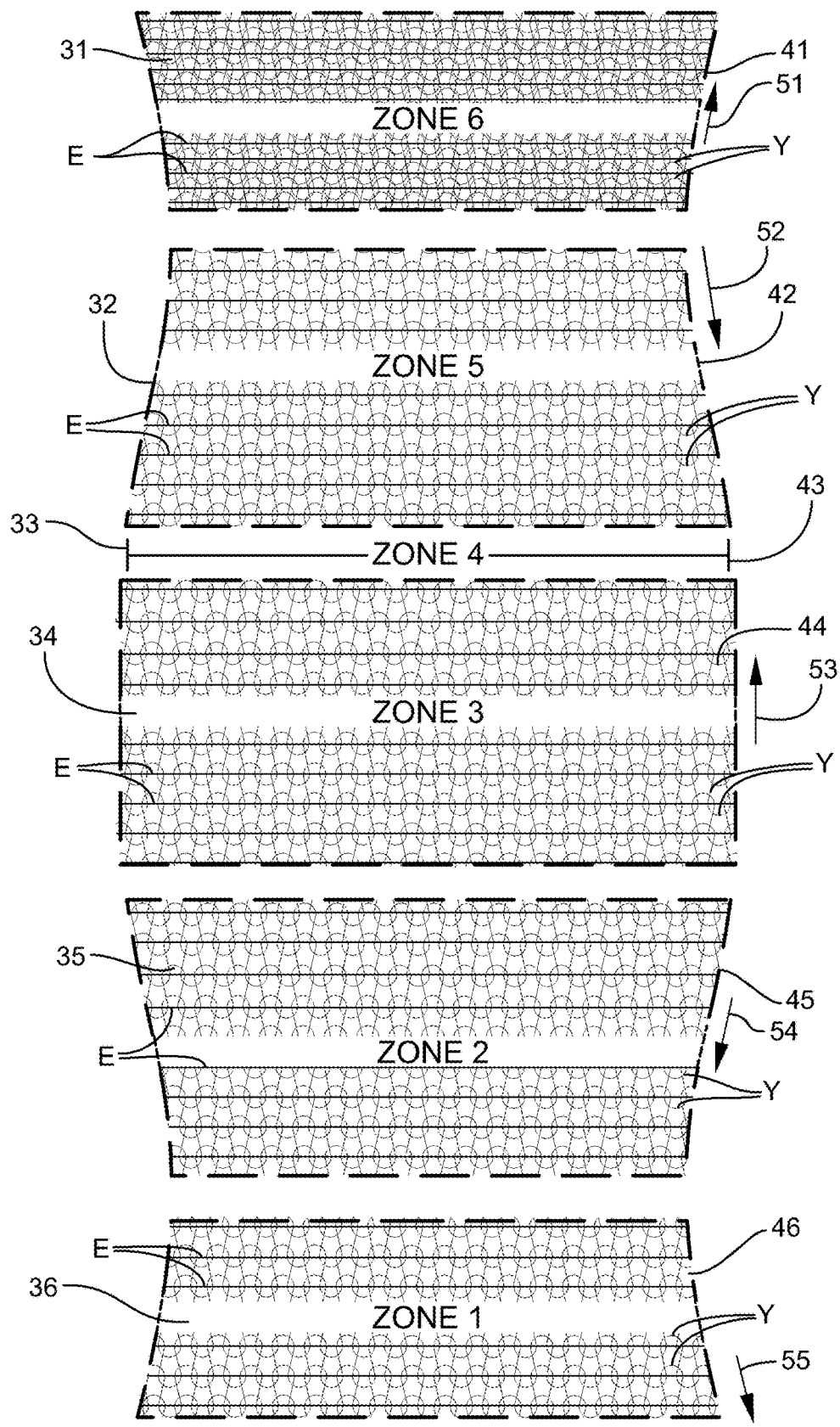
FIG. 8 is a schematic representation of the knit structure in various zones of the exemplary foot garment.

Referring to FIG. 8, targeted compression in the various circumferential zones 41-46 of the foot garment 10 may be graduated by laying-in (or integrating) elastic yarns "E" of strategic lengths with the body yarn "Y" in the different axially-divided garment regions 31-36. In one exemplary embodiment, the knit construction in the first light compression zone 41 (labeled "Zone 6") includes elastic yarns "E" laid-in body yarns "Y", and increasing length in an course-to-course axial or wale-wise direction towards to the open leg end of the garment 10. This reduces compression at the upper ankle region 31 in the direction indicated at arrow 51. Zone 41 may comprise between 20-30 courses of body yarn "Y". The compression in this zone 41 of the garment 10 may be in the range of 10-15 mmHg. The high compression zone 42 (labeled "Zone 5") comprises elastic yarns "E" laid-in the body yarn "Y", and increasing in length in a course-to-course axial direction from the light compression zone 41 towards the compression release zone 43 (labeled "Zone 4"), such that compression is gradually increased as indicated at arrow 52 from the upper ankle region 31 through the lower ankle region 32 of the garment 10. Zone 42 may comprise between 40-60 courses of body yarn "Y". The graduated compression within this zone 42 may be in the range of 20-30 mmHg.

The compression release zone 43 comprises the anatomical turn of the garment 10, and is shaped to closely fit the heel and upper instep of the foot. The garment heel 33B in region 33 has a deep-formed pocket, made via reciprocation (knitting on one side). The upper instep 33A has an oval shaped area of thinner fabric which may also be devoid of elastic yarns to minimize bunching and thickness at the turn of the foot and ankle. Compression in the release zone 43 ("Zone 4") may be less than 15 mmHg.

The high compression zone 44 (labeled "Zone 3") comprises elastic yarns "E" laid-in the body yarn "Y", and having substantially equal lengths in a course-to-course axial direction from the compression release zone 43 towards the moderate compression zone 45 (labeled "Zone 2"). Because of the relative size of the foot in the rear sole and mid-instep region 34, compression is gradually increased as indicated at arrow 53 throughout this region. Zone 44 may comprise between 40-60 courses of body yarn "Y". The graduated compression within the high compression zone 44 may be in the range of 20-30 mmHg. Compression in zones 42 and 44 may be sufficient to create improved function of the venous system, tissue stabilization and lift of the plantar fascia ligaments immediately forward of or adjacent the calcaneus.

The moderate compression zone 45 ("Zone 2") comprises elastic yarns "E" laid-in the body yarn "Y", and decreasing in length in a course-to-course axial direction from the high compression zone 44 towards the light compression zone 46 (labeled "Zone 1"). Zone 45 may comprise between 40-60 courses of body yarn "Y". Compression in this zone 45 is gradually increased as indicated at arrow 54 axially through the front sole and lower instep region 35. The graduated compression within the moderate compression zone 45 may be in the range of 15-20 mmHg. The knit construction in the light compression zone 46 (labeled "Zone 1") includes elastic yarns "E" of increasing length in an course-to-course axial direction towards to the open toe end of the garment 10. This reduces compression at the toe region 36 in the direction indicated at arrow 55. Zone 46 may comprise between 20-30 courses of body yarn "Y". The compression in this zone 46 of the garment 10 may be in the range of 10-15 mmHg.

Referencing the zones designated in FIG. 8, applicant theorizes that varying circumferential compression against the foot can be achieved at different parts of the exemplary garment. This compression is anatomically consistent with the shape of the foot and leg, so that it compresses the venous system and thereby increases flow and velocity of blood return to the upper body, reducing any pooling of fluids which cause swelling, pain and hinder natural recovery. The lift of the foot ligaments is achieved by use of the upper foot rigid bone structure as leverage, while compressing the entire circumference of the foot. This creates lift of the softer under foot tissue. This compression is targeted at just the region in front of the calcaneus where the plantar fascia connects to the heel ("Zone 3"), so the foot ligaments are gently stretched upward toward the upper foot structure. Further structural support is given to the garment's function of lift by concentrated compression just behind the upper heel around the lower Achilles tendon ("Zone 5"). The cooperating compression in Zone 3 and Zone 5 may be sufficiently intense to lift the softer underfoot, but not create restriction and discomfort to the wearer. This may be promoted by lower compressions in the other zones.

For the purposes of describing and defining the present invention it is noted that the use of relative terms, such as "substantially", "generally", "approximately", and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

Exemplary embodiments of the present invention are described above. No element, act, or instruction used in this description should be construed as important, necessary, critical, or essential to the invention unless explicitly described as such. Although only a few of the exemplary embodiments have been described in detail herein, those skilled in the art will readily appreciate that many modifications are possible in these exemplary embodiments without materially departing from the novel teachings and advantages of this invention. Accordingly, all such modifications are intended to be included within the scope of this invention as defined in the appended claims.

In the claims, any means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. Unless the exact language "means for" (performing a particular function or step) is recited in the claims, a construction under § 112, 6th paragraph is not intended. Additionally, it is not intended that the scope of patent protection afforded the present invention be defined by reading into any claim a limitation found herein that does not explicitly appear in the claim itself.

What is claimed:

1. A compression foot garment integrally knit of a body yarn and adapted for wear on a foot of a user, and said compression foot garment comprising a leg end and a toe end, and further comprising:

a first high compression zone axially spaced apart from the toe end of said garment and adapted for applying at least 20 mmHg of substantially circumferential compression to the foot, said first high compression zone comprising elastic yarns integrated with said body yarn, and wherein said foot garment comprises reduced compression axially from said first high compression zone to the toe end of said garment;

a second high compression zone axially spaced apart from the leg end of said garment and adapted for applying at least 20 mmHg of substantially circumferential compression to the foot, said second high compression zone comprising elastic yarns integrated with said body yarn, and wherein said foot garment comprises reduced compression axially from said second high compression zone to the leg end of said garment; and a compression release zone formed at an anatomical turn of said foot garment, and shaped to closely fit a heel and upper instep of the foot, said compression release zone adapted for extending around the foot between said first and second high compression zones for separating said first and second high compression zones, and incorporating a thinner fabric substantially devoid of elastic yarns thereby applying reduced compression to the foot in an area between said first and second high compression zones; and a light compression zone residing adjacent said second high compression zone at the leg end of said garment.

2. The compression foot garment according to claim 1, wherein said first high compression zone comprises elastic yarns adapted for applying course-to-course graduated compression to the foot of the user increasing in an axial direction towards a toe end of said garment.

3. The compression foot garment according to claim 1, wherein said second high compression zone comprises elastic yarns adapted for applying course-to-course graduated compression to the foot of the user increasing in an axial direction towards a leg end of said garment.

4. The compression foot garment according to claim 1, wherein said first and second high compression zones apply substantially equal compression to the foot of the user.

5. The compression foot garment according to claim 1, wherein said first and second high compression zones comprise a substantially equal number of circular-knit courses.

6. The compression foot garment according to claim 1, wherein said compression release zone comprises a reduced compression heel pocket formed between said first and second high compression zones.

7. The compression foot garment according to claim 1, wherein said compression release zone is adapted to extend over a top of the foot proximate an ankle joint of the wearer.

8. The compression foot garment according to claim 1, and comprising a moderate compression zone adjacent said first high compression zone and extending axially towards a toe end of said garment, said moderate compression zone adapted for applying reduced circumferential compression to the foot between said first high compression zone and the toe end of said garment.

9. The compression foot garment according to claim 8, wherein said moderate compression zone comprises elastic yarns integrated with said body yarn, and adapted for applying course-to-course graduated compression to the foot of the user increasing in an axial direction towards the toe end of said garment.

10. The compression foot garment according to claim 8, wherein said moderate compression zone applies between 10%-50% less compression to the foot as compared to the compression applied by said first and second high compression zones.

11. The compression foot garment according to claim 8, wherein each of said first and second high compression zones and said moderate compression zone comprise a substantially equal number of circular-knit courses.

12. The compression foot garment according to claim 8, and comprising a light compression zone residing adjacent said moderate compression zone at the toe end of said garment.

13. The compression foot garment according to claim 1, wherein said light compression zone at the leg end of said garment comprises a folded ankle welt.

14. A compression foot garment integrally knit of a body yarn and adapted for wear on a foot of user, and said compression foot garment having a leg end and a toe end, and further comprising:

a first high compression zone axially spaced apart from the toe end of said garment and adapted for applying at least 20 mmHg of substantially circumferential compression to the foot, said first high compression zone comprising elastic yarns integrated with said body yarn, and wherein said foot garment comprises reduced compression axially from said first high compression zone to the toe end of said garment;

a second high compression zone axially spaced apart from the leg end of said garment and adapted for applying at least 20 mmHg of substantially circumferential compression to the foot, said second high compression zone comprising elastic yarns integrated with said body yarn, and wherein said foot garment comprises reduced compression axially from said second high compression zone to the leg end of said garment; and a compression release zone formed at an anatomical turn of said foot garment, and shaped to closely fit a heel and upper instep of the foot, said compression release zone extending around the foot between said first and second high compression zones for separating said first and second high compression zones, and incorporating a thinner fabric substantially devoid of elastic yarns thereby applying reduced compression to the foot in an area between said first and second high compression zones;

a moderate compression zone adjacent said first high compression zone and extending axially towards a toe end of said garment, said moderate compression zone adapted for applying reduced circumferential compression to the foot between said first high compression zone and the toe end of said garment;

a first light compression zone adjacent said moderate compression zone at the toe end of said garment; and a second light compression zone adjacent said second high compression zone at a leg end of said garment.

15. The compression foot garment according to claim 14, wherein said moderate compression zone applies between 10%-50% less compression to the foot as compared to the compression applied by said first and second high compression zones, and wherein said first and second light compression zones apply between 10%-50% less compression to the foot as compared to the compression applied by said moderate compression zone.

16. The compression foot garment according to claim 14, wherein each of said first and second high compression zones and said moderate compression zone comprise a substantially equal number of circular-knit courses.

* * * * *